(12) United States Patent
Backstein (10) Patent No.: US 9,532,779 B2
(45) Date of Patent: Jan. 3, 2017

(54) SUTURE REMOVAL INSTRUMENT AND METHOD

(71) Applicant: Robert Steven Backstein, Toronto (CA)

(72) Inventor: Robert Steven Backstein, Toronto (CA)

( * ) Notice: Subject to any disclaimer, the term of this patent is extended or adjusted under 35 U.S.C. 154(b) by 163 days.

(21) Appl. No.: 14/472,753

(22) Filed: Aug. 29, 2014

(65) Prior Publication Data

US 2015/0105803 A1  Apr. 16, 2015

Related U.S. Application Data

(60) Provisional application No. 61/890,952, filed on Oct. 15, 2013.

(51) Int. Cl.
*A61B 17/04* (2006.01)
*A61B 17/00* (2006.01)

(52) U.S. Cl.
CPC .. *A61B 17/0467* (2013.01); *A61B 2017/00951* (2013.01)

(58) Field of Classification Search
CPC .............. A61B 17/0467; A61B 2017/0073
USPC ...................... 112/169; 15/104.002
See application file for complete search history.

(56) References Cited

U.S. PATENT DOCUMENTS

| | | | | |
|---|---|---|---|---|
| 2,696,621 A | * | 12/1954 | Miller | B25C 11/00 30/124 |
| 2,998,649 A | * | 9/1961 | Miller | A61B 17/0467 30/131 |
| 3,054,182 A | * | 9/1962 | Whitton, Jr. | A61B 17/0467 30/179 |
| 3,600,806 A | * | 8/1971 | Naccash | A61B 17/0467 30/294 |
| 3,879,846 A | * | 4/1975 | Allen, Jr. | A61B 17/0467 30/124 |
| 3,990,144 A | * | 11/1976 | Schwartz | A61B 17/0467 30/123 |
| 4,384,406 A | | 5/1983 | Tischlinger | |
| 4,494,542 A | | 1/1985 | Lee | |
| D389,619 S | * | 1/1998 | McLeod | D32/35 |
| 7,048,746 B2 | | 5/2006 | Warden et al. | |
| 2014/0243853 A1 | * | 8/2014 | Temple | A61B 17/0467 606/138 |

* cited by examiner

*Primary Examiner* — Julian W Woo
(74) *Attorney, Agent, or Firm* — Nasser Ashgriz; UIPatent Inc.

(57) ABSTRACT

The present device is a suture removal instrument having a disposable guarded blade. The disposable guarded blade comprises of a guard component and a blade component. The present suture removal instrument provides a quick, efficient, and atraumatic removal of the suture. It also decreases discomfort associated with suture removal by severing the suture loop without any need to insert an instrument or part of an instrument into the loop of the tied suture.

5 Claims, 10 Drawing Sheets

SUTURE REMOVAL INSTRUMENT AND METHOD

RELATED APPLICATION

The present invention was first described in U.S. Provisional Patent Application No. 61/890,952 filed on Oct. 15, 2013.

FIELD OF THE INVENTION

The present invention relates generally to surgical equipment, and especially to suture removal tools and methods.

BACKGROUND OF THE INVENTION

Suturing or stitching is the most common method among the many methods for closing cuts and wounds. Sutures can be used on almost every part of the body, internally and externally. Doctors literally "sew" the skin together with individual sutures and tie a secure knot. Sutures then allow the skin to heal naturally when it otherwise may not come together.

Sutures are divided into two general categories: absorbable and non-absorbable. Absorbable sutures rapidly break down in the tissues and lose their strength. This type of suture does not need to be removed. Non-absorbable sutures, on the other hand, maintain their strength for a longer time. These sutures are used to close skin wounds and require removal once the wound has healed. Non-absorbable sutures are made of materials which are not metabolized by the body, and the sutures are removed after healing of the incision or the wound. There are several materials that are used for non-absorbable sutures. A commonly used one is a natural fiber or silk, which has gone through a special manufacturing process to make it adequate for use in surgery. Other non-absorbable sutures are made of artificial fibers, like polypropylene, polyester or nylon; these may or may not have coatings to enhance their performance characteristics.

Many different tools have been developed to remove the non-absorbable suture once the cut is healed. The most common tools used for suture removal are scissors and forceps. To remove a suture, the tail of the suture knot is grabbed by a forceps and lifted to raise the suture loop slightly off the skin. A scissor or other cutter is then used to cut the suture loop, while the forceps removes the suture.

One problem with this method is that it involves the introduction of the tip of one of the scissor blades into the loop of the suture. This requires substantial elevation of the tied loop of the suture away from the skin's surface thereby causing pain to the patient and potentially disrupting the healed incision or cut. Furthermore, the process of introducing a scissor tip into the suture loop requires a certain level of skill and dexterity to be done efficiently, particularly if the patient is anxious or uncooperative. An additional problem with the use of scissors is that the sharp tips and edges can cut or otherwise injure a patient that is anxious or mobile during the suture removal process such as when removing sutures from young children. Other cutting tools commonly used along with forceps to remove sutures include stainless steel scalpel blades which also require the introduction of a cutting surface into the suture loop and therefore have the same problems and disadvantages associated with the use of scissors for suture removal.

In order to eliminate the above mentioned problems, several different suture removal tools have been introduced. Examples of suture removal tools and methods can be found in the U.S. Pat. No. 7,048,746 B2 to Warden et al. and the U.S. Pat. No. 7,699,856 B2 to Van Wyk et al. They introduce a suture removal instrument with a thermal filament tip, which is slipped under the suture in order to heat and cut (i.e., melt off) the suture. The thermal suture removal devices may damage the cut area or cause discomfort or even burn injuries if they touch the skin. Also, since some sutures are made of plastic materials, they can deform when heated. It is more difficult to remove a deformed suture.

SUMMARY OF THE INVENTION

The present invention is a novel suture removal device which allows for a fast and precise removal of sutures with little to no damage or discomfort inflicted on the patient. The new suture removal instrument is unique in both operation and design provides a wide range of functionality for removing stitches after healing. The new device comprises a disposable guarded blade. The cutting edge of the blade is used to cut the suture from the outside surface of a tied suture loop toward the inside surface of said suture loop.

A suture removal instrument for a fast and a precise removal of sutures comprising of a housing comprised of a base and a cover; said base being geometrically symmetric by said cover; said base and said cover having a distal and a proximal end and a top and a bottom, wherein said base being connected to said cover; said base and said cover having a cut-out at said distal end; a blade having a length, a width, a sharp end, and a dull end sandwiched at said distal end of said housing between said base and said cover; and said blade being secured by a securing means; whereby by overlapping said cover on top of said base, said sharp end of said blade being placed in said cut-out providing a guarded blade.

The suture removal instrument of claim 1, further having collecting means to collect removed sutures, wherein said collecting means comprising of an adhesive tape being connected to an interior surface of said base; a window-cut sized approximately smaller than said adhesive tape being located on said cover; a release-paper lining being applied to protect said adhesive tape; and whereby said release-paper lining being removed at the time of use.

The present invention can be easily used for removing any type of non-absorbable or absorbable sutures. The present device is aimed at providing the following objectives.

The first objective of the present invention is to provide a suture removal instrument to decrease discomfort associated with suture removal.

The second objective of the present invention is to provide a suture removal instrument to increase efficiency of suture removal.

The third objective of the present invention is to provide a suture removal instrument with a simple mechanism for suture removal. This is achieved by having a disposable guarded blade.

The fourth objective of the present invention is to provide a suture removal instrument capable of efficient and quick severing of suture material from the outer surface of the suture and without placing a cutting edge or tip inside the tied loop of the suture.

The fifth objective of the present invention is to provide a suture removal instrument that can be used for all suture materials.

The sixth objective of the present invention is to provide a suture removal method having a means to collect removed sutures.

The aforementioned objects of the present invention are attained by a suture removal instrument having a disposable guarded blade and a suture collecting component. Other objects, advantages and novel features of the present invention will become readily apparent from the following drawings and detailed description of preferred embodiments.

BRIEF DESCRIPTION OF THE DRAWINGS

Embodiments herein will hereinafter be described in conjunction with the appended drawings provided to illustrate and not to limit the scope of the claims, wherein like designations denote like elements, and in which:

DETAILED DESCRIPTION OF PREFERRED EMBODIMENTS

Figure 1:
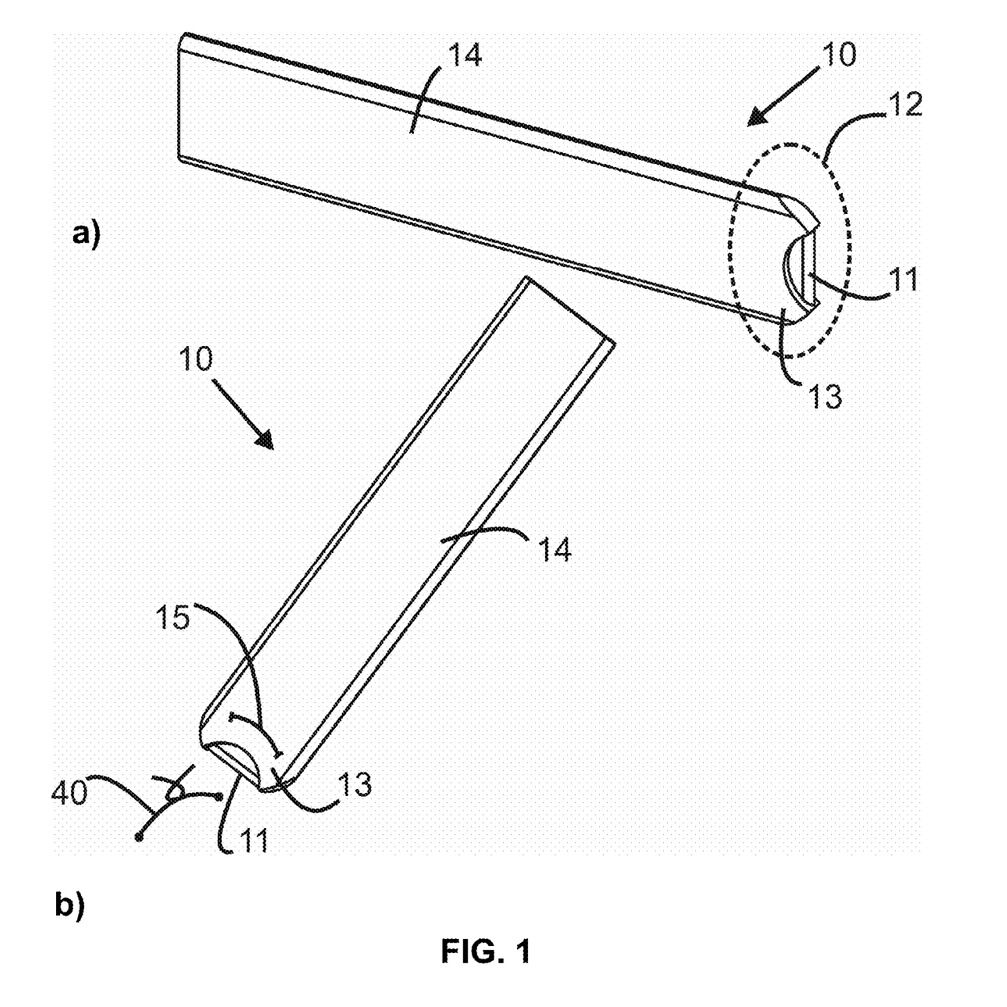
FIG. 1 shows a perspective view of a suture removal instrument.

Referring to FIG. 1 (*a-b*), a suture removal instrument 10 comprises of a guarded blade tip 12 comprising of a cutter or a blade 11 which is embedded in a guard component 13; said guard component 13 also acting as a handle 14 for the instrument 10 to be held in the hand of the operator usually between the tips of the fingers. Embedding the blade 11 inside a guard element 13 minimizes the possibility of injury to the operator and patient due to inadvertent contact with the sharp edge and also provides a means with which to grasp the tool in the hand of the operator without touching the blade 11 component. The blade 11 is placed against the suture 40, and a pressing or slicing action is used to sever the suture 40. The blade 11 sharpness should be enough to easily cut a suture 40 by minimal physical action against the suture material.

Figure 2:
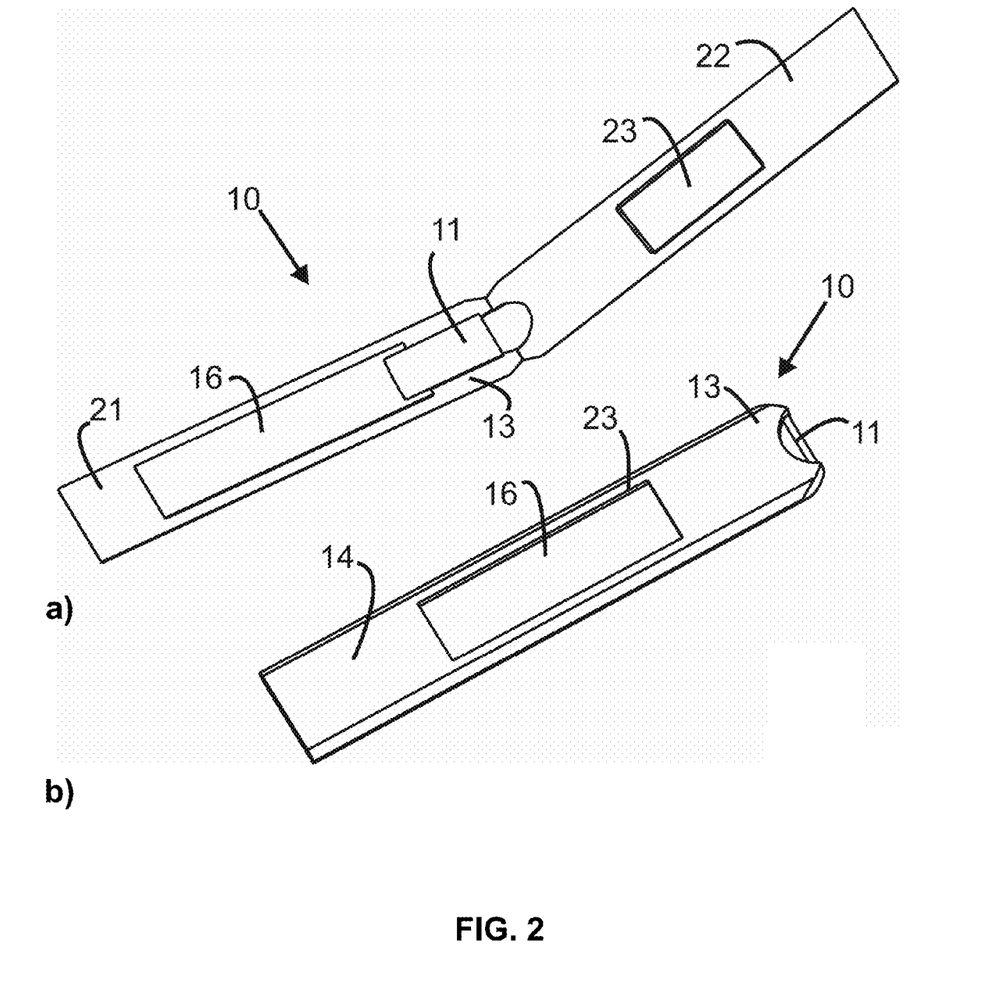
FIG. 2 shows a perspective view of a suture removal instrument and a blade which is sandwiched inside the instrument.

As shown in FIG. 2 (*a-b*), the guard component 13 can be a separate component from the blade 11 in which the blade 11 is embedded, or inserted or it can be an integral component of the blade 11. The latter may be manufactured by having the blade 11 and the guard component 13 made from the same material. In a preferred embodiment, the guard material is flexible so that the angle at which the blade 11 contacts the suture can be easily controlled and changed by the operator and so that the device 10 can be efficiently used on anatomic areas of the body having rounded or otherwise non-planar contours.

FIG. 2 shows a suture removal instrument 10 and a blade 11 which is sandwiched inside the instrument. A housing 14 comprises of a base 21 and a cover 22, wherein the cover 22 has a window-cut 23 to expose an adhesive tape 16. The adhesive tape 16 secures the blade 11 in position and also secures the two sides of the housing 21-22 together in the folded position. The window cut 23 exposes a portion of the internal adhesive tape 16 and this exposed tacky surface is to be used to collect the already removed stitches for easy disposal. A release-paper lining (not shown) is applied over the tacky surface 16 in the window cut 23 to be removed at the time of use.

The blade 11 can be made of any material suitable for surgical applications, preferably of stainless steel or related alloys such as nichrome alloy, tungsten alloy, stainless steel alloy and nickel alloy.

Figure 3:
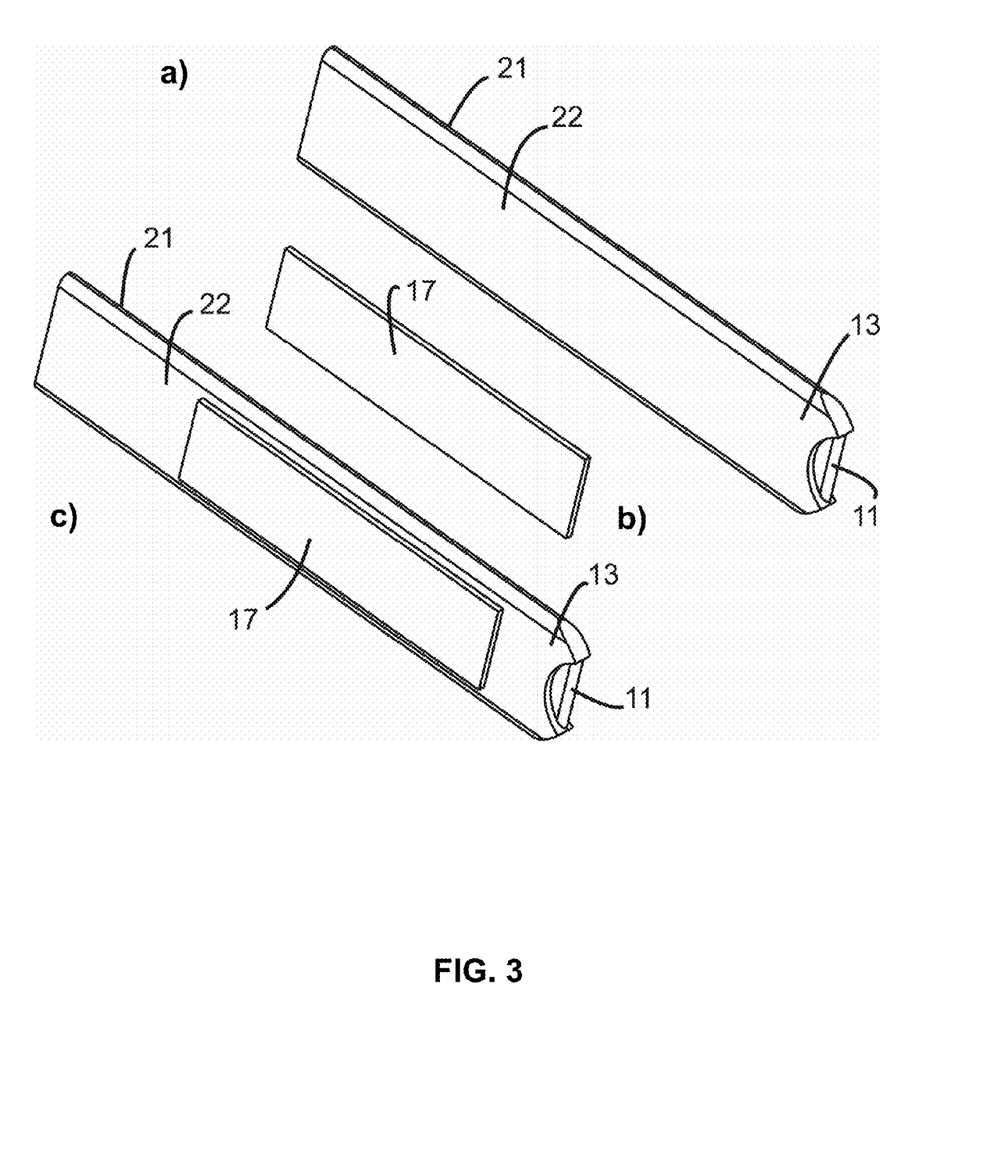
FIG. 3 shows a perspective view of a suture removal instrument having a separate adhesive element.

As shown in FIG. 1-3, the disposable guarded-blade which is used to sever a suture 40, comprises of a metallic sharp blade 11 element encased in a plastic, paper, rubber, metal (or other) guard element 14. The housing of the present invention can be made preferably of a cardboard which is flexible and helps a user to easily sever a suture 40. A part of the cutting edge of the blade element 11 remains uncovered by the guard element 13 by means of a breach 15 in the end of the guard element 13 such that a suture 40 can be severed by the blade 11 while the patient's skin is protected of otherwise sharp edges of the blade 11.

As shown in FIG. 2-3, the present invention further has an element 16 affixed to the guard component 13 or handle 14 that has sticky properties such as a section of adhesive tape, this element 16 serves as a means to collect removed sutures efficiently.

FIG. 2 shows the present invention which comprises of an elongated base housing 21 having a guard component 13, a blade 11 sandwiched between the material of the base housing 21 and a cover 22. An adhesive tape 16 can be attached to the inside part of the base housing 21. A window 23, approximately sized to the adhesive tape 16, is located on the cover housing 22. The adhesive tape 16 which is partially exposed through the window 23 serves as a means to collect removed sutures efficiently.

In other embodiments for the means to collect removed sutures, as shown in FIG. 3, there is no window located in the cover housing 22 but a separate adhesive element 17 such as a segment of double-sided tape is applied to the outer surface of the cover housing 22 to be used as the suture collection element.

Figure 4:
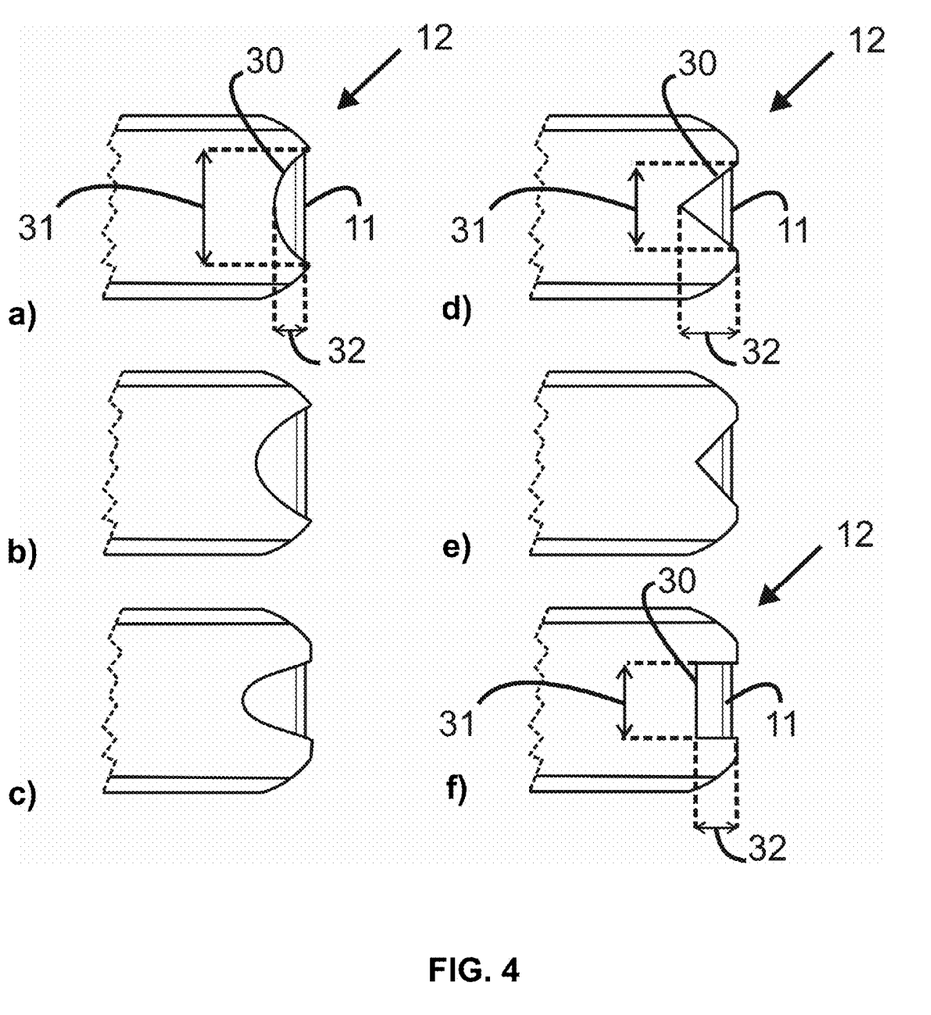
FIG. 4 shows a plurality of suture removal tips with different lengths and depths.

FIG. 4 (*a-f*) shows a plurality of different designs for a guarded blade tip 12. A cut-out 30 which is designed on top of the device to hold a blade 11 has a length 31 and a width 32. The amount of the cutting edge of the blade 11 can vary based on the different lengths 31 and widths 32 of the cut-out 30. The cut-out 30 can be selected from the groups consisting of a circle shape, an oval shape, and a square shape which have different lengths and widths. Pluralities of different designs are shown in FIG. 4 which provide different cutting edges for the blade 11.

Figure 5:
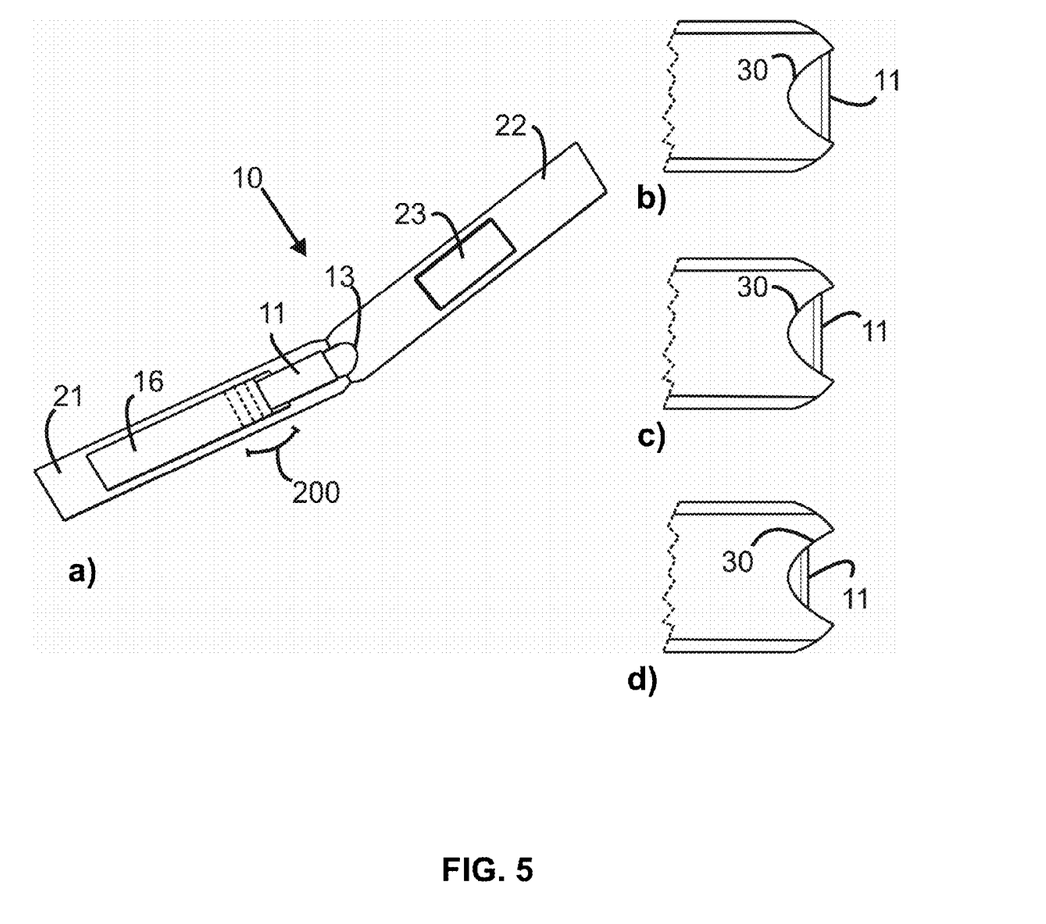
FIG. 5 shows a plurality of suture removal tips with different blade sizes.

FIG. 5 (*a-d*) shows a guarded blade tip 12 which has a blade 11 with different positions inside a cut-out 30. By having different positions in the cut-out 30, the configuration and the length of the blade 11 is changed, so that the device 10 can be efficiently used on areas of the body having rounded or otherwise non-planar contours. FIG. 5 (*a*) shows how the position of the blade can be changed on the base housing 21 by placing the blade in different positions as shown in section 200.

Figure 6:
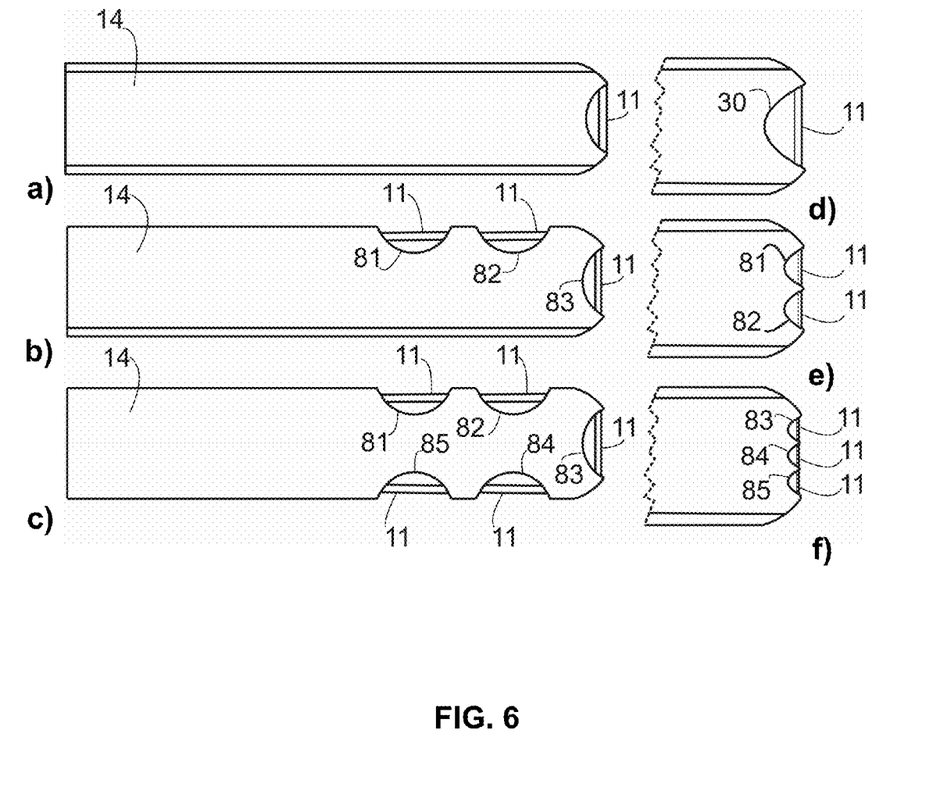
FIG. 6 shows a plurality of suture removal tips having different cut-out.

An additional embodiment for a guarded blade tip 12 is one in which multiple breaches 81-85 are present on the guard component so as to expose a blade 11 or multiple blades edge in a plurality of locations as shown in FIG. 6 (*d-f*). This could be useful in a case of removing a large number of stitches—if the blade is dulling, the operator can use a fresh portion of the blade that is exposed at another breach location.

As shown in FIG. 6 (*a-c*), a suture removal instrument can have a guarded blade which has multiple breaches 81-85 to expose a blade 11 or multiple blades in the upper part and lower part of the housing 14.

Figure 7:
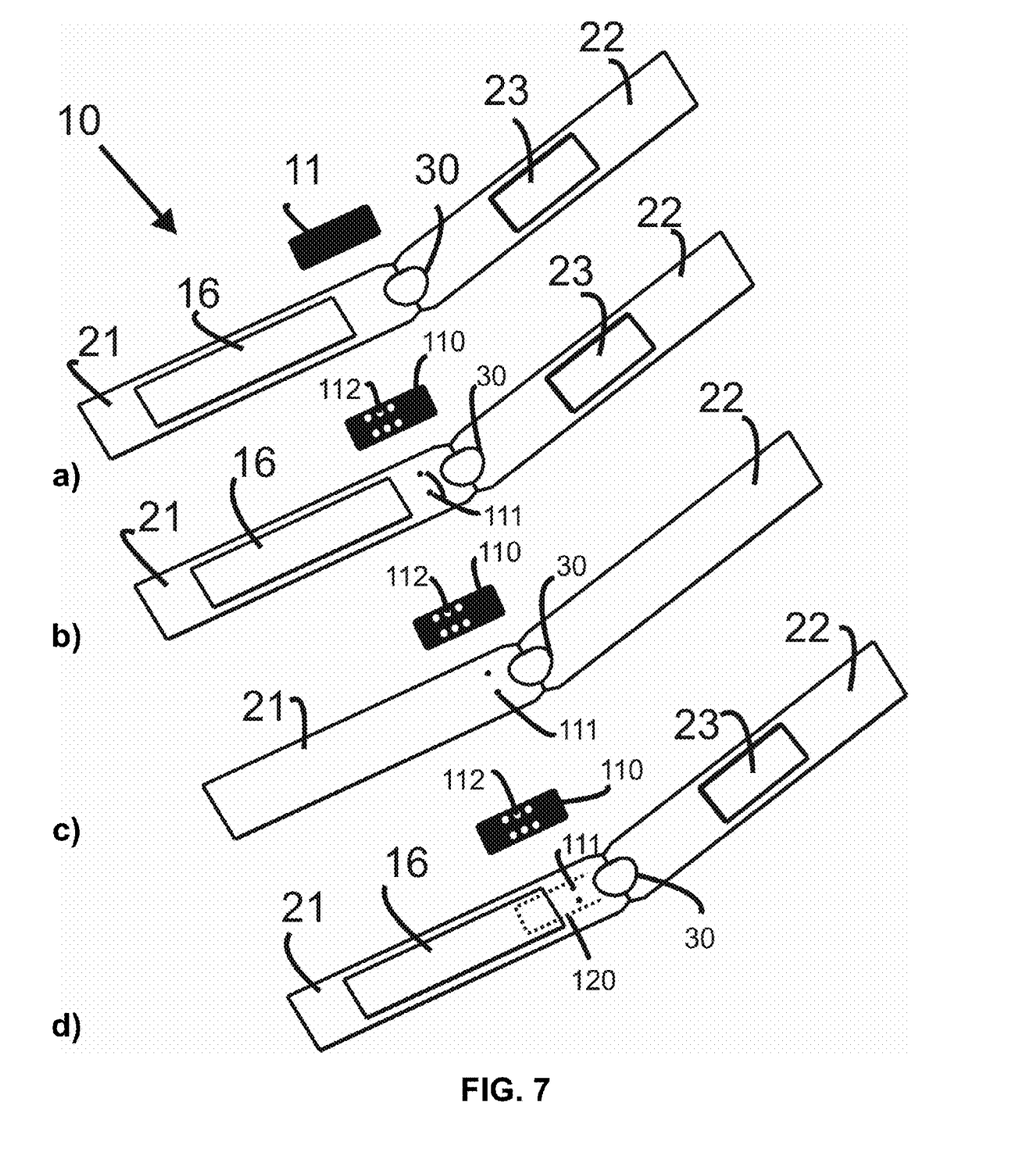
FIG. 7 shows how a blade secures in its place in a suture removal instrument.

As shown in FIG. 7, there is a plurality of methods for securing a blade 11, 110 inside a base housing 21. Using an adhesive tape 16 to secure a blade 11 in a proper position based on the contour of a cut-out 30 is shown in FIG. 7 (*a*). A plurality of apertures 112 designed on a blade 110 sized to be held by a pair of protrusions 111 being used to secure a blade 110 in a proper position based on a contour of a cut-out 30 is shown in FIG. 7 (*b-d*). For a precise securing of a blade 110, combination of the two securing means at the same time can be used (an adhesive tape 16 and a pair of protrusions 111, as shown in FIG. 6 (*b*).

As shown in FIG. 7 (*c*), a blade 110 having a plurality of apertures 112 can be used for securing a blade 110 on a base housing 21. The position of the blade can be adjusted by said apertures 112 present on said blade 110 by aiding said protrusions 111.

As shown in FIG. 7 (*d*), a blade 110 can be secured in a proper position by an adhesive tape 16, a pair of protrusions 111 and a predefined area 130 sized to keep a blade 110.

Figure 8:
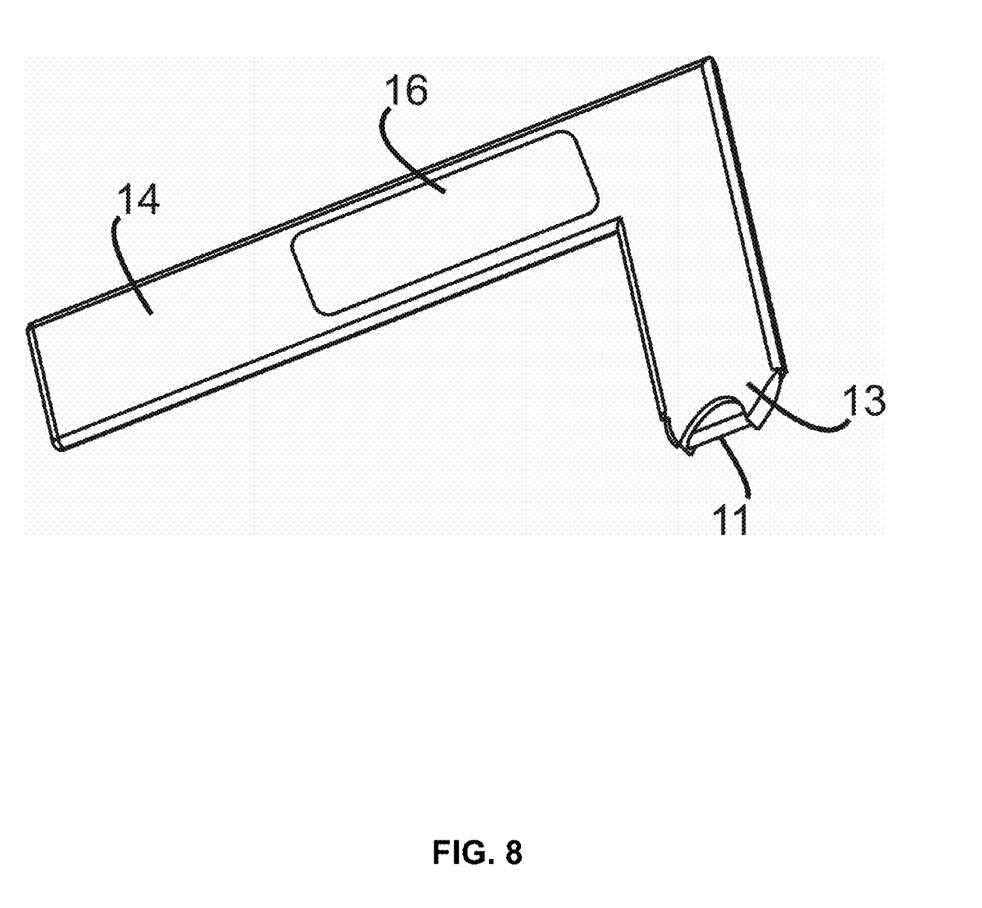
FIG. 8 shows a perspective view of a suture removal instrument having an L-shaped housing.
Figure 9:
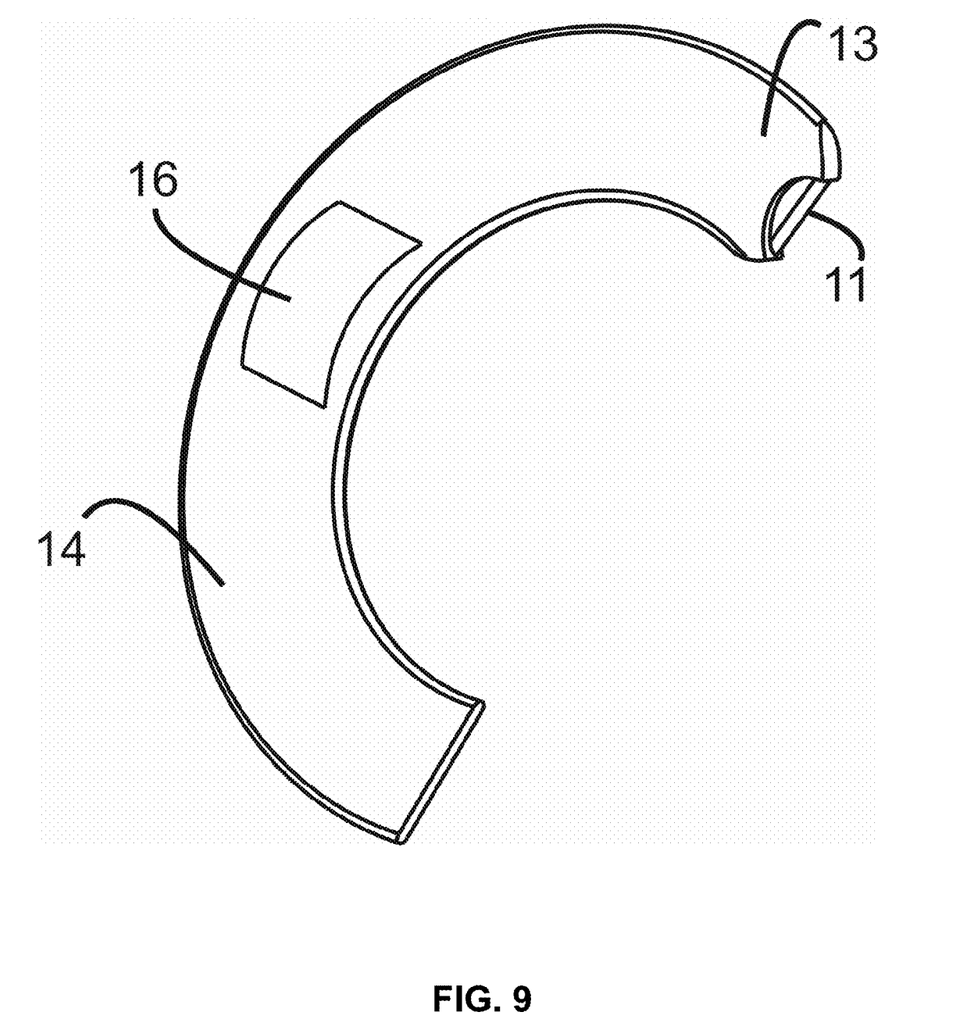
FIG. 9 shows a perspective view of a suture removal instrument having a C-shaped housing.

Other different designs of housing of the present invention to guard a blade 11 inside a guarded blade tip 12 and a handle 14 are shown in FIGS. 8-9. FIG. 8 shows an L-shaped housing having an angled guard component to offer new ergonomics to the user and FIG. 9 shows a C-shaped housing having an arced guard component to facilitate ergonomics. As shown in FIGS. 8-9, an adhesive tape 16 serving as a means to collect removed sutures are present on the handle 14.

In yet another embodiment of the present invention, the blade is affixed or otherwise attached to the guard component by the operator at the time of use and not during the manufacturing process. Many methods are possible to allow attachment of the blade component into the guard component at the time of use including but not limited to a tacky element on a surface of the guard component to which the blade can be adhered, interference-fit mechanisms, clamp mechanisms, and magnetic fixation.

Figure 10:
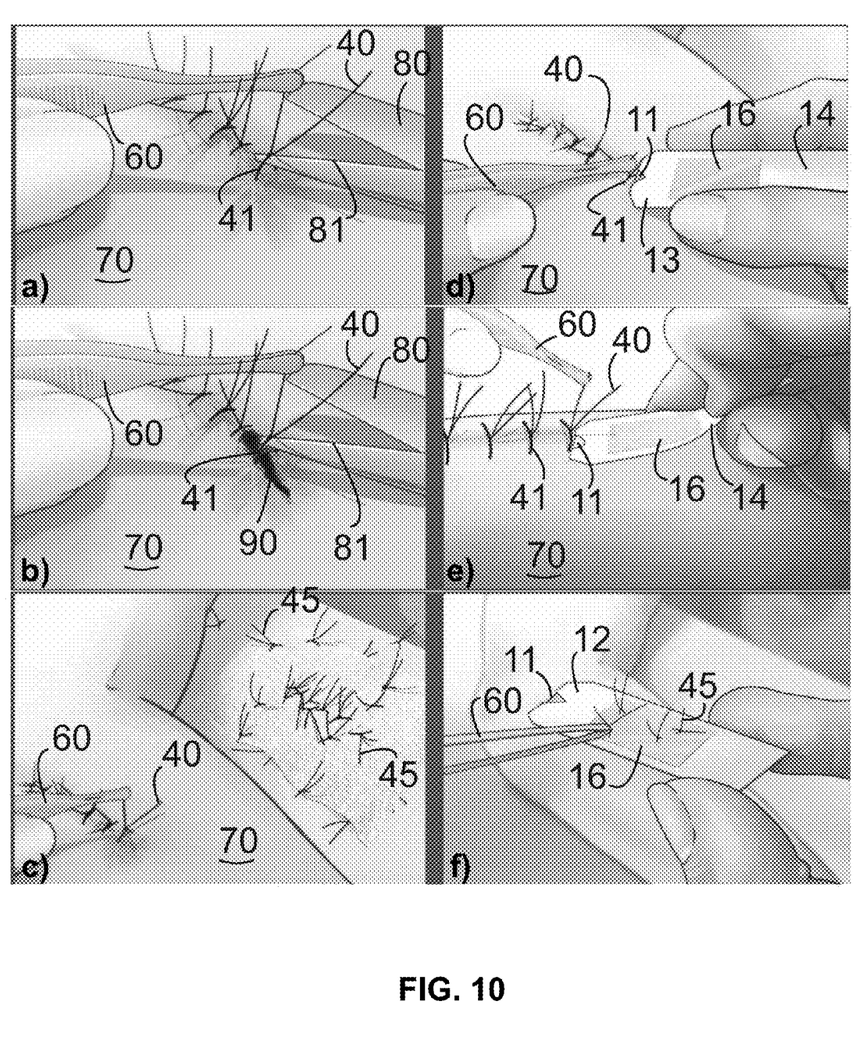
FIG. 10 shows a process of removing a suture with the suture removal instrument and the differences with the conventional method.

As shown in FIG. 10 (*a-f*), the method for cutting a suture 40 using the present device is either by lifting the tail of a tied suture loop 41 using a forceps 60 and using the cutting element of the present device to cut the suture 40 or by pressing the blade 11 against the suture material 40 without the use of a forceps 60. There is no risk of accidentally cutting the patient's skin 70, even if the guarded blade contacts the skin 70 since the guard 12 prevents cutting of any materials which are unable to substantially enter the breach 15 located in the end of the guard component 13. The blade 11 allows for a rapid and effective severing of the suture 40 from the outer surface of the suture 40. Therefore, there is no need to insert a cutting tip 81 inside the tied loop 41 of the suture 40. An adhesive tape 16 serving as a means to collect removed sutures 45 efficiently.

Again referring to FIG. 10 (*a-c*), scissors 80 use an inside-out approach which requires substantial elevation of the knot 41. More tension on the knot 41 causes discomfort to the patient, can disrupt the wound 90, and prolong the procedure. Using scissors 80 precisely can be problematic, especially in the case of a complicated wound 90 or an uncooperative patient. The unguarded tip 81 can disrupt the wound 90 and prolong healing. Traditional suture kits provide no effective means to collect removed sutures 45. Time and effort is wasted after the procedure to maintain a clean workspace.

Again referring to FIG. 10 (*d-f*), outside-in approach requires minimal elevation of the knot 41. Less tension on the knot 41 is more comfortable for the patient and allows the practitioner to work more quickly. Outside-in approach and guarded blade 12 reduce the risk of inadvertent wound damage and patient injury. Patients receive a more comfortable experience and healing time is enhanced. Removed knots 45 are efficiently collected on the tacky surface 16. No cleanup means saved time and a more hygienic workspace.

Other embodiments of the present invention could incorporate a guard component designed to also function as a forceps tool so that the guard component can be used to extract the severed suture from the patient's skin.

Other embodiments of the present invention could incorporate a notch along an edge of the guard component that can be used to capture the tied knot component of the suture so as to facilitate extrication of the severed suture from the patient's skin.

Another embodiment of the present invention is to provide a suture removal instrument which can use a surgical blade which is in the market by having them in different housing sized to keep said a surgical blade in proper position and provide a guarded tip for said surgical blade.

Another embodiment of the present invention is a suture removal instrument in which a base housing can be connected to a cover housing from a distal end of the base and the cover or a proximal end of the base and the cover, or top of the base and the cover, or bottom of the base and the cover.

A variety of methods can be used to manufacture the disposable guarded blade. One method being by injection molding, wherein a metal blade is placed inside a specially designed mold and the material to form the guarded blade is injected into the mold. Another method to manufacture the disposable guarded blade being by folding a guard component over a blade such that a portion of the sharp edge of the blade component is exposed by a breach in the guard component while the remainder of the blade component is covered by the guard component. Another method is to provide the guard and blades as separate components to be attached at the time of use by the operator. The material to form the guarded blade can be plastic or any other material commonly used to manufacture surgical instruments.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

With respect to the above description, it is to be realized that the optimum relationships for the parts of the invention in regard to size, shape, form, materials, function and manner of operation, assembly and use are deemed readily apparent and obvious to those skilled in the art, and all equivalent relationships to those illustrated in the drawings and described in the specification are intended to be encompassed by the present invention.

What is claimed is:

1. A suture removal instrument for a fast and a precise removal of sutures comprising:

a. a housing comprised of a base attached to a cover, wherein said base and said cover are geometrically symmetric and said base has a base-end, a base-outer-surface and base-inner-surface and said cover has a cover-end, a cover-inner-surface and a cover-outer-surface;

b. said base having a base-cut-out at said base-end and said cover having a cover-cut-out at said cover-end;

c. a blade having a length, a width, a sharp end, and a dull end sandwiched between said base and said cover, wherein the sharp end of said blade extends out of said base-cut-out and said cover-cut-out;

d. a securing means securing said blade in the housing, and e. a collecting means to collect removed sutures.

2. A suture removal instrument of claim 1, wherein said collecting means to collect removed sutures comprising:

a. an adhesive tape attached to the base-inner-surface, and b. a window-cut on said cover sized approximately smaller than said adhesive tape to expose said adhesive tape attached.

3. A suture removal instrument of claim 2, further having a release-paper lining to protect said adhesive tape, whereby said release-paper lining is removed at the time of use.

4. A suture removal instrument of claim 1, wherein said collecting means to collect removed sutures comprises of a double-sided adhesive attached to the base-outer-surface or the cover-outer-surface.

5. A suture removal instrument of claim 1, wherein said securing means is an adhesive tape attached to the base-inner-surface to secure said blade from said dull end and a pair of protrusions designed approximately near said base-cut-out to secure a blade having a plurality of apertures sized to grab said pair of protrusions, whereby the blade is positioned in the base-end and that the position of the blade with respect to the base-cut-out is adjustable with said securing means.

\* \* \* \* \*